(12) United States Patent
Weisbeck et al.

(10) Patent No.: US 7,271,116 B2
(45) Date of Patent: Sep. 18, 2007

(54) CATALYST

(75) Inventors: Markus Weisbeck, Köln (DE); Marie-Therese Heinen, Wermelskirchen (DE); Jörg Schmitt, Grevenbroich (DE); Gerhard Wegener, Mettmann (DE); Markus Dugal, Kempen (DE)

(73) Assignee: Bayer MaterialScience AG, Leverkusen (DE)

( * ) Notice: Subject to any disclaimer, the term of this patent is extended or adjusted under 35 U.S.C. 154(b) by 469 days.

(21) Appl. No.: 10/842,994

(22) Filed: May 11, 2004

(65) Prior Publication Data

US 2004/0229747 A1    Nov. 18, 2004

(30) Foreign Application Priority Data

May 15, 2003   (DE) ................. 103 21 876

(51) Int. Cl.
*B01J 29/06* (2006.01)
*B01J 29/89* (2006.01)

(52) U.S. Cl. ............ 502/64; 502/60; 502/62; 502/63; 502/69

(58) Field of Classification Search ........... 502/60, 502/62, 63, 64, 69
See application file for complete search history.

(56) References Cited

U.S. PATENT DOCUMENTS

| 4,833,260 | A |   | 5/1989  | Neri et al. ............ 549/531 |
| 4,937,216 | A | * | 6/1990  | Clerici et al. ........... 502/62 |
| 5,741,749 | A |   | 4/1998  | Crocco et al. .......... 502/56 |
| 5,753,576 | A |   | 5/1998  | Crocco et al. .......... 502/38 |
| 5,912,367 | A |   | 6/1999  | Chang ................. 549/529 |
| 6,008,389 | A |   | 12/1999 | Grosch et al. ......... 549/533 |
| 6,066,750 | A |   | 5/2000  | Chang ................. 549/524 |
| 6,090,961 | A |   | 7/2000  | Hanaoka et al. ........ 556/11 |
| 6,617,465 | B2|   | 9/2003  | Thiele et al. .......... 549/533 |
| 6,740,764 | B1|   | 5/2004  | Chen et al. ........... 549/533 |

FOREIGN PATENT DOCUMENTS

| CA | 2 390 875 | 5/1701 |
| EP |   230 949 | 8/1987 |

OTHER PUBLICATIONS

Applied Catalysis A: 124(2), (month unavailable) 1995, pp. 391-408 M.A. Uguina et al, "Preparation of TS-1 by wetness impregnation of amorphour $SiO_2$-$TiO_2$ solids: influence of the synthesis variables".
J. Phys. Chem. 96, (month unavailable) 1992, pp. 3073-3079, S.P. Mirajkar et al, "Sorption Properties of Titanium Sillicate Molecular Sieves".

* cited by examiner

*Primary Examiner*—Elizabeth D. Wood
(74) *Attorney, Agent, or Firm*—Lyndanne M. Whalen; John E. Mrozinski, Jr.

(57) ABSTRACT

The present invention provides a catalyst containing titanium in bonded form, non-crystalline silicon dioxide and at least one crystalline silicate phase which has a zeolite structure, wherein the non-crystalline silicon dioxide is applied to at least one of the crystalline silicate phases which have a zeolite structure and wherein at least one of the crystalline silicate phases which have a zeolite structure contains silicon-carbon bonds with which non-hydrolytically separable organic groups R are bonded to silicon. Furthermore, the present invention provides a process for preparing this catalyst and a process for producing an epoxide from a compound which contains a carbon-carbon double bond (preferably from propene) comprising reacting the compound which contains a carbon-carbon double bond with hydrogen peroxide in the presence of the catalyst according to the invention.

5 Claims, No Drawings

CATALYST

FIELD OF THE INVENTION

The present invention relates in general to catalysis, and more specifically to a catalyst containing titanium in bonded form, non-crystalline silicon dioxide and at least one crystalline silicate phase which has a zeolite structure, wherein the non-crystalline silicon dioxide is applied to at least one of the crystalline silicate phases which have a zeolite structure, and wherein at least one of the crystalline silicate phases which have a zeolite structure contains silicon-carbon bonds with which non-hydrolytically separable organic groups R are bonded to silicon.

BACKGROUND OF THE INVENTION

It is known from EP-A 0 100 119, EP-A 1 221 442, DE-A 199 54 322 and EP-A 0 904 151 that olefins can be reacted with hydrogen peroxide to give an epoxide when a purely inorganic titanium-containing zeolite is used as catalyst.

However, all these disclosed catalysts have the disadvantage that the oxidizing agent being used (hydrogen peroxide; ethyl- or isopropylbenzene hydroperoxide) decomposes to some extent on these catalysts. The consequences are epoxide yields, with respect to the oxidizing agent, of <100% and in some cases safety-engineering problems due to the formation of molecular oxygen as a decomposition product of the oxidizing agent.

Furthermore, all the disclosed catalysts have the disadvantage that they progressively lose their catalytic activity during the reaction.

The disclosure in WO 99/01445 keeps the desired minimum olefin conversion constant for a limited time by increasing the reaction temperature and/or pressure. The technical limits, however, are very restricted due to the high epoxide reactivity. Even small increases in temperature can markedly reduce the epoxide selectivity. In industrial plants operating on the kiloton scale, small reductions in product selectivity can endanger economic viability.

EP-A 0 743 094 and EP-A 0 790 075 describe thermal regeneration, preferably with molecular oxygen. To achieve target temperatures of 200, better 550° C., in a few cases the catalyst has to be removed from the reactor. At least, it is a common factor in the disclosed regeneration processes that the epoxidation reaction has to be interrupted for the regeneration period.

Short catalyst operating lifetimes result in production losses during the regeneration phase or require a redundant, cost-intensive production pathway. Thus, the development of new catalysts which can achieve high activities with industrially interesting operating lifetimes and high selectivities is desirable.

EP-A 1 221 442 describes regeneration of the titanium zeolite catalyst TS1 with aqueous hydrogen peroxide. The disclosure is characterized in particular in that regeneration can be performed while the epoxide reaction is taking place in a continuous flow system that is in the presence of olefin, methanol and aqueous hydrogen peroxide.

The mechanism of deactivation is not fully understood. Possibly, coating of the catalytically active solid surfaces with organic molecules takes place to such an extent that the active epoxidizing species is no longer available for the desired reaction.

DE-A 199 54 322 describes TS1 molded catalysts which are characterized in that the extrudates are composed of TS1 powder and other materials based on $SiO_2$ for molding purposes. These extrudates, which thus contain crystalline and non-crystalline $SiO_2$ phases, are impregnated with aminopropyltrialkoxysilane and a base, and simultaneously a reagent to modify the surface of the extrudate, and then calcined at 550° C. in a stream of air until no more silicon-carbon bonds can be analytically detected. Although the purely inorganic molded catalysts obtained in this way have the same catalytic activity as similar systems without any silane surface treatment in a reaction step which follows TS1 synthesis, they have the tendency to generate slightly fewer secondary products. In addition the resistance of the strands of extrudate to lateral pressure is about 50% higher. The subsequent reaction of PO with water or methanol to give propylene glycol and methoxypropanol respectively is obviously suppressed a little as compared with disclosed catalysts.

The data in the table given below demonstrate this:

|                       | without modification | with modification |
|-----------------------|----------------------|-------------------|
| methoxypropanol [ppm]: | 3100-3800            | 1700-3200         |
| propanediol [ppm]:     | 400-600              | 300-500           |

For an industrial process, the development of catalysts which achieve longer catalyst operating lifetimes along with still higher epoxide selectivities and epoxide productivities is desirable. Furthermore, it would be desirable to waste less of the expensive oxidizing agent due to decomposition on the catalyst and for use during catalyst regeneration.

To prepare catalysts on an industrial scale (ton scale) the process steps for catalyst preparation should be as reproducible and simple as possible. In order to achieve an economically viable process, the costs of catalyst preparation should be very low.

SUMMARY OF THE INVENTION

Thus, the present invention provides new catalysts for industrial processes which have high activities and do not deactivate while at the same time having excellent selectivities and causing as little loss as possible of oxidizing agent due to decomposition on the catalyst.

The present invention also provides a process for preparing these catalysts.

The present invention further provides a technologically simple liquid phase process for the selective oxidation of hydrocarbons by hydrogen peroxide on these catalysts which leads to high yields and low costs due to high activities, very high selectivities and industrially interesting catalyst operating lifetimes.

The present invention provides an alternative catalyst for the direct oxidation of hydrocarbons, which eliminates, to at least some extent, the disadvantages of known catalysts.

These and other advantages and benefits of the present invention will be apparent from the Detailed Description of the Invention herein below.

DETAILED DESCRIPTION OF THE INVENTION

The present invention will now be described for purposes of illustration and not limitation. Except in the operating examples, or where otherwise indicated, all numbers expressing quantities, percentages and so forth in the specification are to be understood as being modified in all instances by the term "about."

The present invention provides a catalyst containing titanium in elemental or in bonded form, non-crystalline silicon dioxide and at least one crystalline silicate phase which has a zeolite structure, wherein the non-crystalline silicon dioxide is applied to at least one of the crystalline silicate phases which have a zeolite structure, and wherein at least one of the crystalline silicate phases which have a zeolite structure contains silicon-carbon bonds with which non-hydrolytically separable organic groups R are bonded to silicon. Furthermore, the present invention provides a process for preparing this catalyst and a process for producing an epoxide from a compound which contains a carbon-carbon double bond (preferably from propene), comprising reaction of the compound which contains a carbon-carbon double bond with hydrogen peroxide in the presence of the catalyst according to the invention.

The crystalline silicate phase which has a zeolite structure and which contains silicon-carbon bonds, with which non-hydrolytically separable organic groups R are bonded to silicon, is called an organic-inorganic hybrid zeolite.

The organic groups R are preferably present in an amount of 0.01 to 5 wt. %, more preferably 0.1 to 4 wt. % and most preferably 0.3 to 2 wt. %, with respect to the amount of crystalline silicate phases which have a zeolite structure and which contain silicon-carbon bonds with which non-hydrolytically separable organic groups R are bonded to silicon.

When preparing the catalyst according to the invention, calcination is performed at a temperature of 100 to 550° C., more preferably 200 to 450° C.

Thus, the present invention provides in particular compositions containing mainly the elements silicon, titanium, oxygen and carbon, wherein these compositions contain organic silicon-carbon bonds in addition to purely inorganic constituents and, furthermore, the compositions contain at least one crystalline phase in the oxide of silicon oxide with a zeolite structure. The crystalline systems according to the invention, which contain both inorganic and also organic constituents, homogeneously distributed, are called hybrid systems in the present document. The present disclosure details both the synthesis of these hybrid compositions and also the use of these hybrid compositions as catalysts.

Zeolites are crystalline, microporous aluminosilicates, the crystal lattices of which are built up from $SiO_4$ and $AlO_4$ tetrahedra. This structure leads to extremely regularly shaped cavities or channels, the dimensions of which are of the same order of magnitude (0.3-1.5 nm) as the dimensions of many molecules.

The use of aluminum-rich zeolites (A, X or Y) as hydrophilic adsorbents is based on the high polarity which is produced by the presence of aluminum in the lattice. A drop in the aluminum content, by dealumination or, if possible, by appropriate methods of synthesis, leads to a reduction in the polarity of the lattice and thus to an increasingly hydrophobic character for the adsorbent. If the zeolite ZSM-5 is synthesized in the absence of aluminum, silicalite-1, a modification of $SiO_2$ and a typically hydrophobic adsorbent, is obtained.

The incorporation of titanium in the lattice of silicalite-1 increases the polarity again. This leads to an increase in the adsorption capacity for water and to a decrease in the capacity for adsorbing non-polar substances (S. Mirajkar et al., J. Phys. Chem. 96, 3073/3079 (1992)). The hydrophobicity should thus decrease with increasing titanium content. In addition, one should be able to differentiate whether the titanium is incorporated in the lattice or is present as amorphous $TiO_2$ because the latter does not have any effect on the polarity of the lattice.

The titanium atoms, tetrahedrally incorporated in the TS1 (preferably 1.3 mol %), are the so-called active sites. From a catalytic point of view, it would be desirable on the one hand to incorporate more titanium species without forming amorphous $TiO_2$ (as a precipitate) in the silicalite lattice, but on the other hand a catalyst system which is as hydrophobic as possible (achieved by the smallest possible proportion of titanium) greatly increases the adsorption of propene, and above all the desorption of PO, and thus reduces secondary reactions of PO with water to give glycols on the active sites.

Surprisingly, the present invention succeeds in synthesizing a titanium silicalite which is characterized in that non-hydrolysable organic ligands in the $xTiO_2(1-x)SiO_2$ network are homogeneously incorporated so that the stable crystalline structure, with its regularly shaped cavities and channels, is largely retained. The homogeneous incorporation of non-hydrolysable organic ligands is preferably performed by integrating co-condensation agents with non-polar hydrocarbons in the polymer.

In the present document, catalysts according to the invention are called hybrid titanium silicalites or hybrid TS1. Crystallinity is preferred for catalysts according to the invention because the tetrahedral titanium centers then remain stable and catalytically active under the conditions of epoxidation, in particular given the stability of a crystalline lattice.

Furthermore, it is surprising that organic ligands only slightly hinder the forming process of the amorphous arrangement to give a crystalline ZSM-5 structure.

Catalysts according to the invention are particularly characterized in that the decomposition of hydrogen peroxide on these systems is greatly reduced. In many cases, the stability of $H_2O_2$ in the presence of the hybrid TS1 increases by a factor of more than 1.5-2 as compared with conventional purely organic TS1.

Hybrid systems according to the invention with elevated hydrophobicity are especially useful for epoxidation reactions with hydrogen peroxide because hybrid TS1 according to the invention, with its reduced polarity, is obviously targeted towards and precisely adapted to the requirements of the catalytic reaction. Experimentally, it can definitely be demonstrated that the diffusion problems of the non-polar reactants (e.g. olefins such as propene) and the polar products (e.g. PO) are clearly minimized. The hydrophobic character also provides the material with additional stability towards water vapor, which further prolongs the catalyst lifetime.

The synthesis of TS1, first published in 1983 by Clerico (ENICHEM), is sufficiently well-known to those skilled in the art.

Syntheses of the hybrid TS1 in accordance with the invention are based both on the one-step synthesis according to EP-B 0 904 151 and also on the two-step synthesis according to P. Serrano/M. A. Uguina/R. von Grieken/M. Camacho, Appl. catal., A 1995, 124(2), 391-408.

In the classical one-step synthesis, the template molecule (tetrapropylammonium hydroxide as a pattern) is used both for hydrolysis/condensation of the silicon and titanium precursors and also to form the ZSM-5 zeolite structure.

The two-step synthesis, also known as the impregnation method for the synthesis of purely inorganic TS1, is divided into the following two steps:

Step 1: Preparation of an amorphous $SiO_2$—$TiO_2$ sol-gel intermediate product (cogel) of silicon and titanium alkoxides (stable incorporation of Ti(IV)-O-Si species before the actual zeolite synthesis (heterocondensation).

Step 2: Conversion of the amorphous cogel into a zeolite structure by impregnating with a template (tetrapropylammonium hydroxide) followed by hydrothermal synthesis (autoclave reaction).

The hybrid TS1 catalyst is described in the following.

Organic-inorganic hybrid materials, in the context of the invention, preferably contain at least one crystalline phase based on a hybrid $SiO_2/RSiO_x$.

With respect to crystalline silicon dioxide, the main constituent of materials according to the invention, the hybrid systems preferably contain between 0.1 and 4 mol % of titanium, more preferably between 0.5 and 2 mol %, most preferably between 0.8 and 1.6 mol %.

The titanium is preferably present in oxidic form and is preferably incorporated or linked chemically in the organic-inorganic hybrid material via Si—O—Ti bonds. Active catalysts of this type have only very subordinate Ti—O—Ti domains.

In active catalysts, it is preferred that titanium is bonded to silicon via heterosiloxane bonds.

With respect to crystalline silicon dioxide as the base component of the active substance, hybrid systems preferably contain between 0.01 and 5 mol % of non-hydrolysable organic ligands, more preferably between 0.05 and 4 mol %, most preferably between 0.2 and 1.5 mol %. The non-hydrolysable organic ligands are preferably incorporated or linked homogeneously within the organic-inorganic hybrid material.

Homogeneous hybrid compositions according to the invention, containing silicon, titanium and carbon atoms, in a special embodiment in the dried state, can be described approximately by the following formula (I) (residues formed on the surface after modification and optionally incompletely reacted groups are not taken into account here):

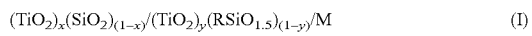
$(TiO_2)_x(SiO_2)_{(1-x)}/(TiO_2)_y(RSiO_{1.5})_{(1-y)}/M$     (I)

In this formula (I), $(TiO_2)_x(SiO_2)_{(1-x)}$ represents purely inorganic crystalline TS1 (MFI crystal structure) or TS2 (MEL crystal structure) and $(TiO_2)_y(RSiO_{1.5})_{(1-y)}$ represents organically modified TS1 (hybrid TS1; as a result of the hybrid TS1 fraction, the entire molecular unit, comprising $xTiO_2(1-x)SiO_2/xTiO_2(1-x)RySiO_{4-y}$, is referred to as hybrid TS1 in the present document).

M in formula (I) is a heteroatom which can be incorporated into the molecular unit in addition to titanium, preferably Sn, Fe, Al, Ge or combinations thereof.

x and y in formula (I) represent the number of oxygen atoms required effectively to saturate the valencies of Si and Ti.

The composition (I) given above can be varied over a wide range.

The specific surface area of the organic-inorganic hybrid materials is not restricted at all. The specific surface area of catalysts in the attached examples is within the range 0.5-100 $m^2/g$. Systems with smaller or larger surface areas, however, are also catalytically active.

Suitable precursor compounds for silicon, titanium and promoter centers are advantageously appropriate low molecular weight organic-inorganic mixed compounds which are suitable for the sol-gel process or a combination of corresponding inorganic and organic-inorganic mixed compounds. Low molecular weight in the context of the invention means monomers or oligomers. Polymeric precursor compounds of silicon, titanium and promoters are also suitable provided they exhibit sufficient solubility.

Preferred solvents for the sol-gel process are alcohols such as isopropanol, butanol, ethanol, methanol or ketones such as acetone, and ethers such as THF or tert.-butyl methyl ether.

Suitable starting materials are in particular all soluble silicon and titanium compounds of the general formula (II) known to a person skilled in the art which can be used as starting materials for the corresponding oxides or hydroxides,

$[R_xM'(OR')_{4-x}]$     (II)

wherein

M' is chosen from silicon and titanium,

R and R' may be identical or different and, independently, may be chosen from $C_1$-$C_{12}$-alkyl and $C_6$-$C_{12}$-aryl, wherein x=0,1,2,3 and R' may also be H.

In a particular embodiment of the organically modified silanes, one or more hydrolyzable groups have been replaced by terminal and/or bridged saturated (e.g. $CH_3$, $C_2H_5$, $C_3H_7$, etc.) or unsaturated (e.g. $C_2H_3$, $C_6H_5$) R groups(s). Polyfunctional organosilanes, e.g. silanols and alkoxides, may also be used. Silanes, organically modified or not, can also be reacted in the presence of dialcohols or polyalcohols such as 1,4-butanediol, to give organically modified polysiloxanes. Bridged R groups (alkylene groups) in the context of the invention are bridged structures such as chain-shaped, star-shaped (branched), cage-shaped or ring-shaped structural elements.

To synthesize catalysts according to the invention, organically modified silicon precursors in which the steric demands of the organic ligands are relatively low, such as e.g. methyltrimethoxysilane, methyltriethoxysilane, methyltriactoxysilane, ethyltrimethoxysilane, ethyl-triethoxysilane or similar precursors, are preferred.

Instead of monomeric alkoxides, their condensation products may also be used. Compositions according to the invention can be used in any physical form for the oxidation reactions, e.g. milled powders, spherical particles, pellets, extrudates, granules.

In a preferred embodiment, the powdered crystalline hybrid TS1 systems are converted into mechanically stable molded items. Molded items are the preferred modification for filling fixed bed reactors such as e.g. tubular reactors. Molded items produced by solidifying shaping processes are sufficiently well known such as e.g. strand extrusion (e.g. extrudates with a diameter of 1-12 mm in accordance with EP-B 0 904 151 or DE-A 199 54 322).

Up to 15 wt. % of binder (with respect to the total weight of calcined or conditioned catalyst) is advantageously mixed with the hybrid TS1 systems according to the invention for strand extrusion purposes. Silicon dioxide, amorphous or crystalline, as a fine powder or as Si precursor compounds (e.g. tetraethoxysilane) is preferred as a non-polar binder. Other binders, such as e.g. are described in EP-B 0 904 151, are suitable provided they do not greatly increase the Lewis acidity of the molded item (Lewis centers can react with functional organic groups, e.g. epoxide functions, and produce secondary products in this way).

To make a dough-like mixture from the material according to the invention, the binder and solvent, e.g. water, alcohol or mixtures thereof, auxiliary substances such as methylcellulose, as is sufficiently well-known from the literature, may be used in small amounts.

The proportion of auxiliary substances, with respect to the total weight, should be preferably less than 5 wt. %, more preferably less than 2.5 wt. %, for materials according to the invention.

The titanium centers are described in the following.

Precursors for the titanium centers are not fixed. For example, titanium alkoxides, titanium salts or organotitanium compounds may be used.

Although any salts of titanium, such as halides, nitrates and hydroxides, can be used, titanium alkoxides, e.g. the butoxide, isopropoxide, propoxide or ethoxide, are preferred.

Titanium derivatives such as tetraalkoxy titanates, with $C_1$-$C_{10}$ alkyl groups such as iso-butyl, tert-butyl, n-butyl, i-propyl, n-propyl ethyl, etc., or titanium alkoxy complexes such as are described in U.S. Pat. No. 6,090,961, e.g. (η5-tetramethyl-cyclopentadienyl)-3-tert-butyl-5-methyl-2-phenoxy)-dimethylsilyl-titanium-dimethoxides or other organic titanium species such as titanyl acetylacetonate, Ti(OSiPh$_3$)$_4$, dicyclopentadienyltitanium dihalide, titanium dihalide dialkoxide, titanium halide trialkoxide, titanium siloxanes such as e.g. diethoxysiloxane-ethyl titanate copolymer (commercially available from Gelest Inc.) are preferably used. Chlorine is preferred as a halogen substituent. Mixed alkoxides of titanium with other elements such as e.g. titanium triisopropoxide-tri-n-butyl stannoxide may also be used. The titanium precursor compounds may also be used in the presence of complex-forming components such as e.g. acetylacetone or ethyl acetoacetate.

To synthesize compositions according to the invention, tetraalkoxy titanates are preferably used as titanium precursors such as e.g. those with $C_2$-$C_6$ alkyl groups such as iso-butyl, tert-butyl, n-butyl, i-propyl, n-propyl, ethyl, are preferred.

Thermal activation is described in the following.

After hydrothermal synthesis compositions according to the invention are preferably activated further by a thermal treatment at 100-500° C. in a variety of atmospheres such as air, nitrogen, hydrogen. The crystalline material according to the invention is preferably dried at 80-120° C. and then heated to 300-500° C. under an inert gas. In some cases it may be advantageous to complete thermal activation at the target temperature, 300-500° C., in an oxygen-containing atmosphere. The calcination temperature and time depend on the target content of organic ligands in the system according to the invention. From 450° C. upwards, burning-off of the organic species, especially in an oxygen-containing atmosphere, takes place to a much larger extent.

Thermally activated (conditioned) hybrid compositions according to the invention frequently exhibit a significantly higher catalytic activity for epoxidation with hydrogen peroxide and a longer catalyst operating lifetime than known purely inorganic TS1 catalysts:

Compositions according to the invention deactivate slowly with time.

Regeneration by washing with hydrogen peroxide solution is known for purely inorganic TS1 systems (for example from EP-A 1 221 442).

Surprisingly, it was found that hybrid systems according to the invention, despite the presence of homogeneously incorporated or appended organic components, can be fully regenerated by washing with hydrogen peroxide solutions (e.g. 3 to 40% strength $H_2O_2$-methanol solution). This finding is all the more surprising because theoretically the organic ligands could also be oxidized by the oxidizing agent hydrogen peroxide. A continuous test trial of 500 hours of epoxidation with hybrid TS1/regeneration of hybrid TS1 on a kilogram scale showed no loss of organic ligands at all (IR analysis of the hybrid TS1 compositions; powder and molded item).

Thus, the composition according to the invention can be used with all hydrocarbons. The term hydrocarbons is understood to include unsaturated or saturated hydrocarbons such as olefins or alkanes and these may also contain heteroatoms such as N, O, P, S or halogens. The organic component to be oxidized can be acyclic, monocyclic, bicyclic or polycyclic and can be monoolefinic, diolefinic or polyolefinic. In the case of organic components with two or more double bonds, the double bonds may be present in conjugated and non-conjugated positions.

Unsaturated hydrocarbons with 2 to 15, more preferably 2 to 10 carbon atoms are preferred, in particular ethene, propene, isobutylene, 1-butene, 2-butene, cis-2-butene, trans-2-butene, 1,3-butadiene, pentene, 1-hexene, other hexenes, hexadiene, cyclohexene, benzene.

The process parameters are described in the following.

Hybrid TS1 catalysts are preferably used in liquid phase reactions for the partial oxidation of hydrocarbons in the presence of hydrogen peroxide. Hybrid TS1 catalysts are also active in the gas phase.

The process parameters for the hydro-oxidation reaction in the liquid phase can be varied over a wide range.

HO catalysts according to the invention operate in particular at temperatures of 30 to 200° C., more preferably 40 to 80° C. and in particular at 40 to 70° C.

For economic and structural apparatus reasons it is often advantageous to operate under elevated reaction pressures for liquid phase reactions. The heterogeneous catalysts according to the invention exhibit particularly high catalytic activity in the pressure range from atmospheric pressure to 70 bar. A pressure range of 2 to 35 bar is more preferred, most preferably 5 to 30 bar.

The residence time may also be varied over a wide range. The residence time is preferably <70 seconds. Hybrid TS1 molded catalysts exhibit particularly high catalytic activities with good selectivities with residence times <90 sec. Very short residence times, in the lower range of seconds (<40 seconds), are also provided by the present invention.

The feed composition is described in the following.

Hybrid TS1 catalysts are preferably used in liquid phase reactions for the partial oxidation of hydrocarbons in the presence of hydrogen peroxide.

In this way, epoxides are obtained from olefins, ketones are obtained from saturated secondary hydrocarbons, and alcohols are obtained from saturated tertiary hydrocarbons, preferably selectively.

The molar amounts of hydrocarbon used, with respect to the total number of moles of hydrocarbon, diluent gas, hydrogen peroxide and solvent, and the relative molar ratios of the components may be varied over a wide range. An excess of hydrocarbon is preferably used with respect to the oxygen used (on a molar basis). The hydrocarbon content is typically greater than 1 mol % and less than 80 mol %. Hydrocarbon contents in the range 4 to 90 mol % are more preferably used, most preferably in the range 8 to 70 mol %. The hydrocarbon contents may be in an amount ranging between any combination of these values, inclusive of the recited values.

The oxygen may be used in a variety of forms such as molecular oxygen, air, nitrogen oxide, hydrogen peroxide. Molecular oxygen is preferred.

The molar proportion of oxygen, with respect to the total number of moles of hydrocarbon, oxygen, hydrogen and diluent gas, can be varied over a wide range. The oxygen is preferably used in a molar deficiency with respect to the hydrocarbon. 1-30 vol. % of oxygen is preferably used, more preferably 5-25 vol. % of oxygen.

In the absence of hydrogen, molded items according to the invention exhibit only low activity and selectivity. Up to 180° C., the productivity in the absence of hydrogen is generally low; at temperatures above 200° C., large amounts of carbon dioxide are formed in addition to partial oxidation products.

Any known source of hydrogen can be used, such as pure hydrogen, cracker hydrogen, synthesis gas or hydrogen from the dehydrogenation of hydrocarbons and alcohols. In an embodiment of the invention, the hydrogen may also be produced in situ in a downstream reactor, e.g. by dehydrogenation of propane or isobutane or alcohols such as e.g. methanol or isobutanol. Hydrogen may also be introduced into the reaction system as a complex bonded species, e.g. a catalyst-hydrogen complex.

The proportion by volume of hydrogen peroxide, with respect to the total volume, made up mainly of the components methanol/water/hydrogen peroxide/hydrocarbon, can be varied over a wide range. Typical hydrogen peroxide contents are 10-40 vol. %, more preferably 15-40 vol. %, most preferably 17-30 vol. %.

A diluent gas such as e.g. nitrogen, helium, argon, methane, carbon dioxide, carbon monoxide or similar mainly inert gases, may optionally be added to the essentially required reactant gases described above. Mixtures of the inert components described may also be used. Other inert hydrocarbons, such as for example fluorinated hydrocarbons (hexafluoroethane, $CF_4$, and others), may also be used as components to dilute the feed gas or circulating gas. The added inert component is beneficial to transportation of the heat being evolved in this exothermic oxidation reaction and frequently for safety-engineering reasons.

HO catalysts according to the invention have a large economic advantage over the prior art. Furthermore, systems according to the invention exhibit a much longer catalyst lifetime than traditional purely inorganic titanium silicalite catalysts.

Catalysts according to the invention can be prepared easily and cost-effectively from a chemical engineering point of view on an industrial scale.

The present invention is explained in more detail by the following examples. The present invention is not restricted to these examples.

EXAMPLES

Instructions for Testing HO Molded Catalysts (Test Instructions)

A 250 ml BÜCHI glass autoclave was used under a semi-batch mode of operation, this having been conditioned using a thermostat (oil). The reactor was provided continuously with feed gases using a set of two mass flow regulators (propene, nitrogen). For the reaction, 0.2 g of hybrid TS1 powder catalyst, suspended in a methanol/water mixture (15 g of methanol, 5 g of 30% strength hydrogen peroxide solution in water), were initially introduced at 50° C. and 3 bar. A SWAGELOK pressure retention valve ensured that the pressure was kept constant. The suspension was stirred at 800 rpm using a magnetic stirring core. The reactant gases were introduced directly into the suspension through a 1 mm 0.2 mm capillary (immersion). The standard active substance loading was 21 l of gas/(g TS1*h). To perform the oxidation reaction with 0.2 g of TS1, the following stream of gas, referred to as the standard gas composition in the following, was chosen: 0.252 l/h of $C_3H_6$, 3.96 l/h of $N_2$ (corresponding to 6% propene in $N_2$).

For the sake of simplicity, in the following orientating trials only the PO vol. % concentration in the emerging stream of gas was detected quantitatively using GC analysis; the amount of PO dissolved in the liquid phase was taken into account in a qualitative evaluation. (PO is the abbreviation for propylene oxide).

The reaction gases were analyzed quantitatively using gas chromatography. Gas chromatographic separation of the individual reaction products was performed using a combined FID/WLD method involving passage through three capillary columns.

FID: HP-INNOWax, 0.32 mm internal diameter, 60 m length, 0.25 μm layer thickness.

WLD: Sequential arrangement of

HP-Plot Q, 0.32 mm internal diameter, 30 m length, 20 μm layer thickness

HP-Plot molecular sieve 5 Å, 0.32 mm internal diameter, 30 m length, 12 μm layer thickness.

The abbreviations are defined as follows:

| | |
|---|---|
| FID: | Flame ionization detector |
| WLD: | Thermal conductivity detector |
| HP-Plot Q: | Gas chromatography column from Hewlett-Packard (fused silica; PLOT = porous layer open tubular) |
| HP-Plot molecular sieve 5 Å: | Gas chromatography column from Hewlett-Packard (molecular sieve, 5 Angstrom; PLOT = porous layer open tubular) |

Synthesis of Hybrid TS1 by the Two-Step Process

The concentration of non-hydrolyzable organic ligands was 0.5 mol %, with respect to silicon dioxide.

The following substances were used as starting materials:

| | |
|---|---|
| Si sources: | Tetraethyl orthosilicate (TEOS, from Merck) Methyltrimethoxysilane (MTMS from Merck) |
| Ti source: | Tetrabutyl orthotitanate (TBOT from Aldrich) |
| Template: | Tetrapropylammonium hydroxide (TPAOH from SACHEN, HH) |
| Water: | Cation-free water (cations < 10 ppm) |

| Reactants | Amount used |
|---|---|
| TEOS | 137.78 g |
| MTMS | 0.46 g |
| HCl, 0.05 mol/l | 47.8 g |
| TBOT | 5.72 g |
| Isopropanol | 33.3 g |
| TPAOH (base) | 10-12 ml |
| TPAOH (template) | 32 g |

Hydrolysis of the Silicon Component

TEOS and MTMS were initially introduced into a 250 ml round-bottomed flask and stirred well, then the aqueous HCl solution was metered in over the course of 5 minutes and the mixture was stirred for about 1 hour. A maximum temperature of 69° C. was reached after 39 minutes. After complete hydrolysis of the TEOS, the mixture was cooled to 1-2° C. in an ice bath; this process took about 40 minutes.

Incorporation of the Titanium Species in the Network

A solution of 5.72 g of TBOT, dissolved in 33.3 g of isopropanol, was now metered into the mixture very slowly, using a syringe pump. At a rate of 11 ml/h, the metering process took 4.5 hours. Care was taken to ensure that the temperature of the mixture did not rise above 3° C. and that the mixture was stirred at maximum intensity because otherwise the precipitation of anatase is favored. After completing addition of the titanium component, the clear solution had to be stirred for a further 1 hour under the same conditions in order to ensure complete condensation of the titanium species in the hybrid network. After that time, the free TiOH groups were fully saturated with silicates so the reaction could be accelerated without risk of the production of an anatase precipitate. The clear solution was then heated to room temperature (RT) over the course of 30 minutes.

Basic Gelling Process

About 10 ml of 20% strength TPAOH solution was metered into the well-stirred mixture, using a syringe pump, at a rate of addition of 10 ml/h. After 32 minutes, the gel point was reached. Over the course of a further 10 minutes, the clear gel changed from a flexible structure to a brittle structure. After a further 60 minutes the gel material was crushed in the mixer and then dried for 12 hours at 110° C. and under 300 mbar pressure in a drying cabinet. The dried gel was then crushed to 100-160 μm in a mortar.

Zeolite Formation 20 g of the dried and crushed powder were placed in an autoclave lined with Teflon, intensively blended with 32 g of 20% strength TPAOH solution (1.6 times the amount by weight) (the powder has to be uniformly wetted with liquid) and placed in a drying cabinet for 12 hours at 170° C. under the naturally produced pressure (hydrothermal synthesis). After cooling to RT, the contents of the reactor were rinsed out of the reactor with fully deionized water and the solid phase was separated from the liquid phase in a centrifuge (5 min, 3000 rpm). The solid was then washed three times with 30 ml of alkali-free fully deionized water. After washing, the product was dried for 4 hours at 110° C. and then conditioned and calcined in two variants:

Hybrid TS1 550: the dried amorphous hybrid gel was heated to 550° C. in a muffle furnace under a stream of $N_2$ (250 l/h) over the course of one hour. The product was then held at 550° C. for a further hour under a stream of $N_2$ and then calcined at 550° C. for 15 hours with the supply of air (100 l/h).

Hybrid TS1 400short: the dried amorphous hybrid gel was heated to 400° C. in a muffle furnace under a stream of $N_2$ (250 l/h) over the course of one hour. The product was then held at 400° C. for a further hour under a stream of $N_2$ and then cacined at 400° C. for 15 hours with the supply of air (100 l/h).

Hybrid TS1 400long: the dried amorphous hybrid gel was heated to 400° C. in a muffle furnace under a stream of $N_2$ (250 l/h) over the course of one hour. The product was then held at 400° C. for a further hour under a stream of $N_2$ and then calcined at 400° C. for 30 hours with the supply of air (100 l/h).

Example 1

For reaction, 0.2 g of hybrid TS1 550 powdered catalyst, suspended in a methanol/water mixture (15 g of methanol, 5 g of 30% strength hydrogen peroxide solution in water), were initially introduced at 50° C. and 3 bar. The suspension was stirred at 800 rpm using a magnetic stirrer core. The reactant gases were introduced directly into the suspension via a 1 mm 0.2 mm capillary (immersion). To perform the oxidation reaction with 0.2 g of catalyst, 0.252 l/h of $C_3H_6$ and 3.96 l/h of $N_2$ (corresponding to 6% propene in $N_2$) were bubbled into the liquid phase.

In a test performed in accordance with the test instructions, a constant PO selectivity of 95% was achieved. The PO concentration in the emerging gas phase was 5%. The rate of PO production remained the same until the $H_2O_2$ concentration in the liquid phase had dropped to below 4%.

Example 2

For reaction, 0.2 g of hybrid TS1 400short powdered catalyst, suspended in a methanol/water mixture (15 g of methanol, 5 g of 30% strength hydrogen peroxide solution in water), were initially introduced at 50° C. and 3 bar. The trial was performed in the same way as in example 1.

In a test performed in accordance with the test instructions, a constant PO selectivity of 95% was achieved. The PO concentration in the emerging gas phase was 6.1%. The rate of PO production remained the same until the $H_2O_2$ concentration in the liquid phase had dropped to below 4%.

Example 3

For reaction, 0.2 g of hybrid TS1 400long powdered catalyst, suspended in a methanol/water mixture (15 g of methanol, 5 g of 30% strength hydrogen peroxide solution in water), were initially introduced at 50° C. and 3 bar. The trial was performed in the same way as in example 1.

In a test performed in accordance with the test instructions, a constant PO selectivity of 95% was achieved. The PO concentration in the emerging gas phase was 6.5%. The rate of PO production remained the same until the $H_2O_2$ concentration in the liquid phase had dropped to below 4%.

Example 4

Cyclohexene was chosen instead of propene as an unsaturated hydrocarbon. A catalyst analogous to the one in example 3 was used for the partial oxidation of cyclohexene. Cyclohexene was continuously introduced into the liquid phase with the aid of an evaporator.

In a test performed in accordance with the test instructions, a constant epoxide selectivity of 93% was achieved. The epoxide concentration in the emerging gas phase was 4%. The rate of cyclohexene oxide production remained the same until the $H_2O_2$ concentration in the liquid phase had dropped to below 5%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A catalyst comprising:
    a) titanium in bonded form;
    b) non-crystalline silicon dioxide; and
    c) at least one crystalline silicate phase having a zeolite structure, wherein the non-crystalline silicon dioxide is applied to at least one of the crystalline silicate phases having a zeolite structure and at least the titanium atoms tetrahedrally incorporated in one crystalline silicate phase, and wherein at least one of the crystalline silicate phases having a zeolite structure contains silicon-carbon bonds binding non-hydrolytically separable organic groups R to silicon.

2. A catalyst according to claim 1 further comprising:

d) additional silicon, in elemental or in bonded form, which is not present in the form of non-crystalline silicon dioxide and is also not present in the form of a crystalline silicate phase having a zeolite structure.

3. The catalyst according to claim 1, wherein at least one of the crystalline silicate phases having a zeolite structure has a zeolite structure chosen from MFI, MEL, BEA, MOR and a mixed structure thereof.

4. The catalyst according to claim 1, wherein the crystalline silicate phase having silicon-carbon bonds is an organically modified glass and contains terminal and/or bridging organic groups in the crystalline network.

5. The catalyst according to claim 1, wherein the organic groups R are present in an amount of about 0.01 to about 5 wt. %, with respect to the amount of the crystalline silicate phases having a zeolite structure and contain the silicon-carbon bonds with which non-hydrolytically separable organic groups R are bonded to silicon.

* * * * *